United States Patent [19]  [11] 4,064,268
Adolphi et al.  [45] Dec. 20, 1977

[54] HALOBENZOYLPROPIONATE AND N,N-DIETHYL-M-TOLUAMIDE AS INSECT REPELLENTS

[75] Inventors: Heinrich Adolphi, Limburgerhof; Gerhard Bachmann, Frankenthal, both of Germany

[73] Assignee: BASF Aktiengesellschaft, Ludwigshafen (Rhine), Germany

[21] Appl. No.: 697,438

[22] Filed: June 18, 1976

[30] Foreign Application Priority Data

July 5, 1975 Germany .................. 2530070

[51] Int. Cl.$^2$ .................. A01N 9/20; A01N 9/24
[52] U.S. Cl. .................. 424/308; 424/324; 424/DIG. 10

[58] Field of Search .......... 424/308, 324, DIG. 10

[56] References Cited

U.S. PATENT DOCUMENTS 2,932,665  4/1960  Wagner .................. 260/558 R

FOREIGN PATENT DOCUMENTS 1,923,916  11/1970  Germany.

*Primary Examiner*—Allen J. Robinson
*Attorney, Agent, or Firm*—Keil, Thompson & Shurtleff

[57] ABSTRACT

Inspect repellents containing as active compound a composition of a halobenzoylpropionate and N,N-diethyl-m-toluamide.

2 Claims, No Drawings

HALOBENZOYLPROPIONATE AND N,N-DIETHYL-M-TOLUAMIDE AS INSECT REPELLENTS

The present invention relates to insect repellents containing as active compound a composition of a halobenzoylpropionate and N,N-diethyl-m-toluamide.

The use of insectifuges continues to grow in interest. The advantage of these agents, which are not toxic to insects and other arthropods, is that they in no way disturb the biological balance and cause no damage to beneficial creatures.

Numerous substances are already known which prevent insects from settling on the treated surfaces, e.g., the skin of human beings or animals. However, these substances only have an effect on a small number of pests.

For instance, N,N-diethyl-m-toluamide (U.S. Pat. No. 2,932,665) has a particularly good action on mosquitos, but its effect on flies is poor.

It is also known (German Laid-Open Application DOS No. 1,923,916) that halobenzoylpropionates have a very strong repellent action on flies, but their action on mosquitos is not always satisfactory.

We have now found that compositions consisting of a halobenzoylpropionate of the formula

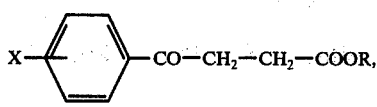

where X denotes halogen and R denotes straight-chain or branched-chain alkyl of from 1 to 4 carbon atoms which may be substituted by chloro or methoxy, and N,N-diethyl-m-toluamide of the formula

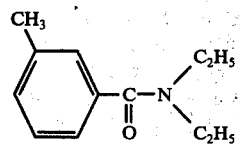

have a much stronger repellent effect than that obtained by adding the actions of the individual components.

Further advantages are that the composition is almost odorless and is not harmful to the skin. Articles of clothing are not dyed. The agents are effective for up to 24 hours after application.

The compositions according to the invention may be used in undiluted form or as formulations containing from 0.5 to 80 wt%, preferably 2 to 40 wt%, of active ingredient composition.

Suitable forms of application are solutions, emulsions, suspensions, dusts, creams and sprays. The forms of application depend entirely on the purpose for which the agents are being used; in any case they should ensure a fine distribution of the active ingredient.

For the preparations of solutions to be sprayed direct, hydrocarbons such as tetrahydronaphthalene, and alkylated naphthalenes may be used. Aqueous formulations may be prepared from emulsion concentrates, pastes and wettable powders by adding water. To prepare emulsions, the ingredients as such or dissolved in a solvent may be homogenized in water or organic solvents by means of wetting or dispersing agents, adherents or emulsifiers. Concentrations which are suitable for dilution with water may be prepared from active ingredient, emulsifying or dispersing agent and possibly solvent. Suitable solvents are for example alcohols, especially those miscible with water, and polyethylene oxides.

Dusts may be prepared by mixing or grinding the active ingredients with a solid carrier. Talc is particularly suitable for preparing powders.

Cream preparations may be based on vaseline, glycerol, lanolin, zinc oxide, etc.

For use in spray form the active ingredient composition may be filled into aerosols together with a solubilizer and a conventional propellant.

The ratio of the active ingredients to each other is generally in the range of from 10:1 to 1:10, preferably 6:1 to 1:6, parts by weight.

The agents according to the invention are effective on injurious and troublesome articulata such as insects, ticks and mites. The following are repelled: Aedes and Anopheles species, especially mosquitos, e.g., *Aedes aegypti, Aedes rusticus, Aedes communis, Aedes caspius, Aedes taemiorrhynchus, Aedes detritus, Aedes dorsalis, Aedes sollicitans, Aedes vexans, Anopheles maculipennis, Anopheles quadrimaculatus, Anopheles bancrofti, Culex pipiens, Culex fatigans,* and *Culex quinquefasciatus,* flies, e.g., *Stomoxys calcitrans, Musca domestica, Fannia canicularis* and *Siphona irritans,* Simuliidae, e.g., *Simulium reptans, Simulium ornatum, Simulium maculatum* and *Simulium damnosum,* bugs, e.g., *Rhodnius prolixus, Cimex lectularius* and *Triatoma infestans,* lice, especially *Pediculus humanus,* fleas, especially *Pulex irritans, Ctenocephalides felis, Ctenocephalides canis* and *Xenopsylla cheopis,* ticks, especially *Ixodes ricinus, Rhipicephalus sanguineus, Boophilus microplus, Boophilus annulatus, Argas persicus, Ornithodorus moubata* and *Ornithodorus megnini,* and mites, e.g., *Trombicula autumnalis* and *Trombicula akamushi.*

Suitable substituents for R in the general formula for the halobenzoylpropionates are straight-chain or branched-chain alkyl radicals of 1 to 4 carbon atoms optionally substituted by chloro or methoxy. Preferred substituents are methyl, ethyl, n-propyl, isopropyl, n-butyl, isobutyl, sec-butyl, tert-butyl, 2-methoxyethyl and 2-chloroethyl. The benzoyl radical is substituted by halogen, e.g., chlorine, bromine and iodine, preferably bromine.

The following examples demonstrate the use of the agents. They were carried out with ethyl β-(p-bromobenzoyl)-propionate (I) and N,N-diethyl-m-toluamide (II).

EXAMPLE 1

Action on *Aedes aegypti*

An area 3 × 3 cm is shaved on the back of a guinea pig, and uniformly treated with the active ingredient formulation. The amount of formulation used in each case is 0.5 ml. The formulation contains the individual active ingredient, or the composition in a weight ratio of 1:1 and 1:3, in a concentration of 0.25 wt% in a 1:1 mixture of ethanol and glycerol.

The guinea pig is then arranged in a fixed position (head protected) on the side of a cage (50 × 50 × 50 cm) containing from 1,000 to 2,000 mosquitos (*Aedes aegypti*).

After 2 minutes the number of mosquitos which have punctured the shaved area of skin is counted. The animal is then removed from the cage, and the test repeated after 1 and 2 hours.

| Active ingredient | I | I + II (1:1) | I + II (1:3) | II | Control |
|---|---|---|---|---|---|
| immediately | 0 | 0 | 0 | 0 | 40 |
| 60 mins. | 2.5 | 0 | 0 | 0 | 40 |
| 120 mins | 7.5 | 0.75 | 0.75 | 2.0 | 40 |

The active ingredient composition is clearly superior to its individual constituents.

EXAMPLE 2

Action on *Rhodnius prolixus*

Rabbits whose stomachs have been shaved are placed, after an area 10 × 10 cm in size has been uniformly treated with 1 ml of active ingredient formulation, in a coop. The formulation contains the individual active ingredient, or the compositions in a weight ratio of 3:1, 1:1 and 1:3, in a concentration of 0.5 wt% in a 1:1 mixture of ethanol and glycerol.

The animals used for the experiment are bugs of the penultimate larval stage; there are 20 famished animals in each of the usual breeding vessels with a gauze cover. In one series they are immediately applied after treatment, and in another series 60 minutes after treatment.

After the jars have been applied the number of bugs sucking blood is recorded over a 10-minute period.

| Active ingredient | I | I + II (3:1) | I + II (1:1) | I + II (1:3) | II | Control |
|---|---|---|---|---|---|---|
| Immediate application | 2.5 | 6.5 | 4 | 3 | 3 | 8 |
| Application after 60 mins. | 14.5 | 12.0 | 10 | 9 | 15 | 20 |

It is apparent from this table that the active ingredient compositions repel the bugs to a far greater extent than their individual components.

EXAMPLE 3

Action on ticks

Rabbits whose stomachs have been shaved are placed, after an area 10 × 10 cm in size has been uniformly treated with 1 ml of active ingredient formulation, in a coop. The formulation contains the individual active ingredient, or the compositions in a weight ratio of 3:1 and 1:3, in a concentration of 0.5 wt% in a 1:1 mixture of ethanol and glycerol.

The animals used for the experiment are ticks after the third molt. The vessels, each containing 20 ticks, are flat plastic dishes with a gauze cover. The vessels are applied 60 minutes after the rabbits have been treated. In the next 10 minutes the number of ticks sucking blood is recorded.

| Active ingredient | I | I + II (3:1) | I + II (1:3) | II | Control |
|---|---|---|---|---|---|
| After 60 mins. | 17 | 5 | 5 | 10 | 18 |

These figures show that the active ingredient compositions repel ticks better than their individual components.

We claim:

1. A repellent composition adapted for use against insects, ticks and mites and containing the halobenzoylpropionate of the formula

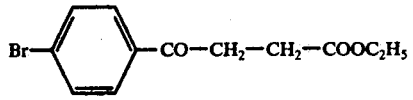

and N,N-diethyl-m-toluamide of the formula

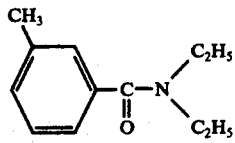

wherein the weight ratio of halobenzoylpropionate to N,N-diethyl-m-toluamide is from 3:1 to 1:3.

2. A process for repelling insects, ticks and mites which comprises treating the skin or clothing exposed to settling by insects, ticks or mites thereon with an insect-, tick- or mite-repelling amount of a repellent composition as claimed in claim 1.

* * * * *